United States Patent
Fremy et al.

(10) Patent No.: US 8,987,519 B2
(45) Date of Patent: Mar. 24, 2015

(54) PROCESS FOR PREPARING DIALKYL DISULPHIDES

(75) Inventors: Georges Fremy, Sauveterre de Bearn (FR); Jean-Michel Raymond, Cauneille (FR)

(73) Assignee: Arkema France, Colombes Cedex (FR)

( * ) Notice: Subject to any disclaimer, the term of this patent is extended or adjusted under 35 U.S.C. 154(b) by 0 days.

(21) Appl. No.: 13/877,016

(22) PCT Filed: Sep. 30, 2011

(86) PCT No.: PCT/FR2011/052285
§ 371 (c)(1),
(2), (4) Date: Jun. 18, 2013

(87) PCT Pub. No.: WO2012/042184
PCT Pub. Date: Apr. 5, 2012

(65) Prior Publication Data
US 2013/0267739 A1 Oct. 10, 2013

(30) Foreign Application Priority Data

Sep. 30, 2010 (FR) ..................................... 10 57904

(51) Int. Cl.
C07C 321/28 (2006.01)
C07C 321/24 (2006.01)
C07C 319/28 (2006.01)
C07C 319/24 (2006.01)

(52) U.S. Cl.
CPC ............. *C07C 319/28* (2013.01); *C07C 319/24* (2013.01)
USPC ............................................... 568/26; 568/21

(58) Field of Classification Search
USPC ....................................................... 568/21, 26
See application file for complete search history.

(56) References Cited

U.S. PATENT DOCUMENTS

| | | |
|---|---|---|
| 5,312,993 A | 5/1994 | Arretz |
| 2001/0976726 | 6/2001 | Georges Fremy |

FOREIGN PATENT DOCUMENTS

| | | |
|---|---|---|
| EP | 0 446 109 | 9/1991 |
| EP | 0 976 726 | 2/2000 |

OTHER PUBLICATIONS

International Search Report for PCT/FR2011/052285 dated Dec. 2, 2011.

*Primary Examiner* — Paul A Zucker
*Assistant Examiner* — Mark Luderer
(74) *Attorney, Agent, or Firm* — RatnerPrestia

(57) ABSTRACT

The present disclosure relates to a process for obtaining dialkyl disulphides from alkyl mercaptan and from sulphur, in which a reaction intermediate present in the final disulphide is decomposed at the end of synthesis. This operation makes it possible to avoid the degradation of said reaction intermediate over time, which is responsible for the decrease in purity of the dialkyl disulphide.

19 Claims, 1 Drawing Sheet

PROCESS FOR PREPARING DIALKYL DISULPHIDES

CROSS REFERENCE TO RELATED APPLICATIONS

This application is the U.S. National Phase application of PCT International Application No. PCT/FR2011/052285, filed Sep. 30, 2011, and claims priority to French Patent Application No. 1057904, filed Sep. 30, 2010, the disclosures of which are incorporated by reference in their entirety for all purposes.

FIELD OF THE INVENTION

The present invention relates to the field of organic disulphides and polysulphides (subsequently referred to as "organic sulphides") and more particularly to that of dialkyl disulphides, in particular dimethyl disulphide (DMDS), and in particular to the process for preparing same.

BACKGROUND OF THE INVENTION

Organic sulphides are widely used in a very large number of fields in the chemical industry and in particular the petrochemical industry. In particular, dimethyl disulphide is used as an agent for sulphiding catalysts for the hydrotreatment of petroleum feedstocks, as a feedstock additive for steam cracking, to cite just a few of the possible uses of this compound.

Compared with other products used in these applications, for instance commercial di-tert-alkyl polysulphides, organic sulphides, and in particular DMDS, have many advantages, in particular a high sulphur content (68%) and non-coking degradation products ($CH_4$, $H_2S$ in the case of DMDS). Furthermore, in these applications, DMDS results in performance levels that are generally superior to other commercial products normally used, for example di-tert-alkyl polysulphides.

Among the known methods for the synthesis of organic sulphides, a particularly efficient and economical method is the oxidation of alkyl mercaptans with sulphur, for example for the synthesis of DMDS, the oxidation of methyl mercaptan with sulphur according to the following reaction:

$$2CH_3SH + S \xrightarrow{\text{catalyst}} \underset{\text{DMDS}}{CH_3SSCH_3} + H_2S$$

methyl mercaptan

This oxidation of alkyl mercaptans with sulphur, catalysed by organic or inorganic, homogeneous or heterogeneous, basic agents under batchwise or continuous conditions, is accompanied by a release of hydrogen sulphide and also of dialkyl polysulphides (for example dimethyl polysulphides $CH_3S_xCH_3$ in the case of the synthesis of DMDS) with a sulphur rank x of greater than 2.

In order to manufacture DMDS according to this process of oxidation with sulphur with high yields and a limited production of DMPS (dimethyl polysulphides with a rank greater than 2), patent EP 0 446 109 describes a preparation process comprising two reaction regions interrupted by an intermediate degassing region and followed by a distillation region, in order to eliminate the unwanted by-products.

Although giving a good performance level in terms of yield and selectivity for DMDS, it turns out that this process results in a final product comprising a not insignificant amount of methyl hydrodisulphide ($CH_3SSH$). This amount generally varies between approximately 200 ppm and approximately 800 ppm, in particular when high DMDS productivities are sought.

The result of this impurity, which can be considered to be a reaction intermediate, is a slow decomposition over time to give methyl mercaptan and dimethyl trisulphide, by reaction with dimethyl disulphide, according to the following reaction:

$$CH_3SSH + CH_3SSCH_3 \rightarrow CH_3SH + CH_3SSSCH_3$$

The instability of methyl hydrodisulphide ($CH_3SSH$, CAS No.: 6251-26-9) is, moreover, mentioned in the literature by H. Bohme and G. Zinner, in "Justus Liebigs Annalen der Chemie", 585, (1954), 142-9, in which the methyl hydrodisulphide $CH_3SSH$ decomposes at ambient temperature, by reacting with itself, to give dimethyl trisulphide and $H_2S$ according to the reaction:

$$2CH_3SSH \rightarrow H_2S + CH_3SSSCH_3$$

In the case of the synthesis of DMDS by oxidation with sulphur, the very low concentrations of $CH_3SSH$ do not enable this product to react with itself, and the reaction with the product predominantly present in the medium, DMDS, is highly favoured.

The increase in the methyl mercaptan content in the DMDS makes the synthesis of DMDS described in application EP 0 976 726 not very cost effective, owing to the volatile impurities in the DMDS (traces of methyl mercaptan and traces of dimethyl sulphide (DMS)) which are eliminated in an additional distillation step.

Indeed, its impurities give DMDS a very unpleasant and aggressive odour, which is regarded as a significant cause of trouble during the handling of this product by users.

However, the DMDS obtained, freed of the volatile impurities, still contains traces of $CH_3SSH$. In addition, the simple elimination of the impurities by distillation results in considerable DMDS yield losses. This is because $CH_3SSH$ is much less volatile than methyl mercaptan and than DMS, and has a boiling point of 108° C. very close to that of DMDS (boiling point between 107° C. and 110° C. at ambient pressure). These products (DMDS and $CH_3SSH$) are therefore very difficult to separate.

The main objective of the present invention is therefore to provide a process which makes it possible to reduce, or even to eliminate to a very large extent as far as completely, the alkyl hydrodisulphide impurity, for example $CH_3SSH$ in the case of the synthesis of DMDS.

Another objective of the present invention is a process for eliminating the alkyl hydrodisulphide impurity, without a significant loss of dialkyl disulphide yield.

SUMMARY OF THE INVENTION

One aspect of the present invention relates to a process for treating a reaction crude containing a majority of a dialkyl disulphide obtained by oxidation of at least one alkyl mercaptan with sulphur in an industrial apparatus, in which process said reaction crude is brought into contact with at least one basic catalyst.

According to another aspect, the present invention relates to a process for preparing dialkyl disulphide, said process comprising at least the following steps:

a) oxidation of an alkyl mercaptan with sulphur, by basic catalysis, so as to obtain a first reaction crude containing predominantly the corresponding dialkyl disulphide;

b) stripping of the H₂S formed;
c) distillation of the residual alkyl mercaptan;
d) separation of the heavy products (polysulphides);
e) final topping making it possible to eliminate the last traces of the volatile compounds;
f) bringing the stream exiting step a), better still exiting step b), preferably exiting step c), more preferably exiting step d), or exiting step e), into contact with a basic catalyst enabling the elimination of the alkyl hydrodisulphide by conversion of said alkyl hydrodisulphide to dialkyl sulphide or dialkyl polysulphides; and
g) recovering of the dialkyl disulphide containing a low alkyl hydrodisulphide content.

Another aspect of the present invention consists of a method of increasing the overall productivity of the industrial synthesis of dialkyl disulphides of formula RSSR, in which R is defined as above, comprising the contacting at least one basic catalyst with the reaction crude of oxidation of an alkyl mercaptan of formula RSH with sulphur.

DETAILED DESCRIPTION OF THE INVENTION

Figure 1:
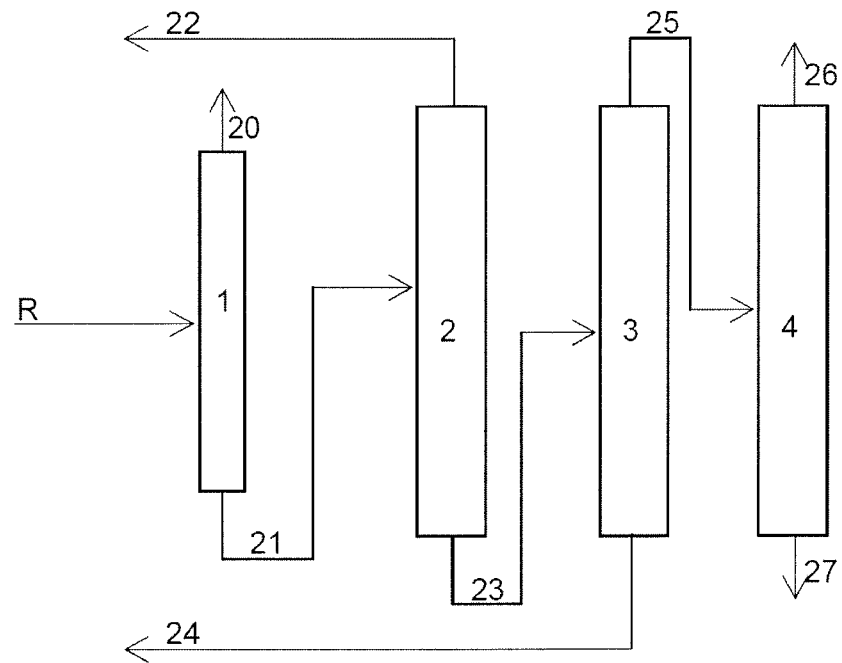
FIG. 1 is a schematic diagram of an industrial apparatus for purifying a dialkyl disulphide synthesis reaction crude.

It has now been found, surprisingly, that the rate of decomposition of alkyl hydrodisulphide in the presence of corresponding dialkyl disulphide can be greatly increased by passage over a basic catalyst of a reaction crude comprising predominantly said dialkyl disulphide.

In the rest of the present description, the expression "reaction crude comprising predominantly a dialkyl disulphide" is intended to mean a reaction medium in which the oxidation of at least one alkyl mercaptan with sulphur has been carried out by basic catalysis.

Preferably, the reaction crude is a reaction crude from which the hydrogen sulphide has been separated (for example by distillation, stripping, and the like). More preferably, the reaction crude is a reaction crude from which the alkyl mercaptan that has not reacted has also been separated (for example by distillation).

Advantageously, the reaction crude is a reaction crude from which not only the hydrogen sulphide and the residual alkyl mercaptan, but also the ("heavy") polysulphides, and also optionally the traces of alkyl mercaptan and of alkyl sulphide, are separated, for example by distillation.

Thus, a first aspect of the present invention relates to a process for treating a reaction crude containing a majority of a dialkyl disulphide obtained by oxidation of at least one alkyl mercaptan with sulphur in an industrial apparatus, in which process said reaction crude is brought into contact with at least one basic catalyst. The term "alkyl mercaptan" is intended to mean a compound of formula RSH, in which R represents a linear or branched alkyl radical containing from 1 to 20 carbon atoms, preferably from 1 to 10 carbon atoms, more preferably from 1 to 6 carbon atoms, and more preferentially from 1 to 4 carbon atoms. The alkyl radical R may also be substituted with one or more groups, which may be identical or different, chosen from halogens, amino, alkylamino, dialkylamino, carboxyl, alkylcarbonyloxy, alkoxycarbonyl, hydroxyalkyl, alkoxy, mercaptoalkyl, alkylthio, alkylcarbonylamino and alkylaminocarbonyl.

Preferably, R represents a linear or branched, unsubstituted alkyl radical containing from 1 to 10 carbon atoms, preferably from 1 to 6 carbon atoms, more preferably from 1 to 4 carbon atoms. In at least one embodiment, the alkyl mercaptan is methyl mercaptan.

The term "dialkyl disulphide" is intended to mean a compound of formula RSSR, in which R is as defined above. In at least one embodiment, the dialkyl disulphide is dimethyl disulphide (DMDS).

The process according to the invention is thus particularly suitable for the synthesis of dimethyl disulphide, without any loss of yield, with elimination of the impurity methyl hydrodisulphide. The elimination of the hydrodisulphide is carried out by means of at least one basic catalyst.

The basic catalyst may be of any type known to those skilled in the art. Said basic catalyst is preferably heterogeneous with respect to the reaction medium, so as to facilitate its subsequent separation. Thus, the basic catalyst may, for example, be chosen from anion exchange resins, such as Amberlyst® A21 from Rohm & Haas, basic catalysts in free amine form, aluminas doped with sodium oxide and/or with potassium oxide, magnesium oxide (MgO), and the like. Preferably, the basic catalyst is an anion exchange resin.

The reaction for basic catalysis of the reaction crude is carried out in a separate step subsequent to the synthesis by oxidation with sulphur. In other words, the reaction crude is used, advantageously after having been subjected to one or more purifications such as those subsequently described, in a further step consisting of a basic catalysis which makes it possible to eliminate the impurity alkyl hydrodisulphide RSSH, in which R is as defined above, in particular CH₃SSH, without any significant loss of dialkyl disulphide, in particular dimethyl disulphide, yield.

The inventors have in fact discovered, surprisingly, that it is possible to greatly accelerate the rate of decomposition of the alkyl hydrodisulphide, in the presence of the corresponding dialkyl disulphide, in particular the rate of decomposition of methyl hydrodisulphide, in the presence of dimethyl disulphide, in a subsequent and separate basic catalysis reaction.

According to one preferred embodiment, the basic catalyst used for reducing the alkyl hydrodisulphide content, of the reaction crude comprising predominantly alkyl disulphide, is of the same type as, or even is identical to, the basic catalyst used for the reaction for oxidation of the alkyl mercaptan with sulphur so as to give said reaction crude comprising predominantly dialkyl disulphide.

According to another aspect, the present invention relates to a process for preparing dialkyl disulphide, said process comprising at least the following steps:
a) oxidation of an alkyl mercaptan with sulphur, by basic catalysis, so as to obtain a first reaction crude containing predominantly the corresponding dialkyl disulphide;
b) stripping of the H₂S formed;
c) distillation of the residual alkyl mercaptan;
d) separation of the heavy products (polysulphides);
e) final topping making it possible to eliminate the last traces of the volatile compounds;
f) bringing the stream exiting step a), better still exiting step b), preferably exiting step c), more preferably exiting step d), or exiting step e), into contact with a basic catalyst enabling the elimination of the alkyl hydrodisulphide by conversion of said alkyl hydrodisulphide to dialkyl sulphide or dialkyl polysulphides; and
g) recovering of the dialkyl disulphide containing a low alkyl hydrodisulphide content.

The expression "low alkyl hydrodisulphide content" is intended to mean a content generally less than 50 ppm by weight, preferably less than 10 ppm by weight, more preferably less than 5 ppm by weight.

The process, described above, for synthesis of dialkyl disulphide is particularly suitable for the synthesis of dialkyl disulphide of the general formula RSSR, in which R is as defined above. Said process is entirely suitable for the synthesis of dimethyl disulphide.

Step a) of the process, described above, for oxidation of alkyl mercaptan with sulphur is carried out in a conventional manner known to those skilled in the art. This step is, for example, described in patent application EP 0 976 726. For example, step a) can be carried out under hot conditions and under pressure, for example between 20° C. and 100° C., under 2 to 15 bar, typically, for example, at approximately 70° C., under approximately 6 bar in the case of the oxidation of methyl mercaptan with sulphur.

Steps b), c), d) and e) are included as purification steps, i.e. steps for the at least partial and ideally total elimination of the unwanted by-products present in the reaction crude obtained at the end of step a). More specifically, each of steps b), c), d) and e) corresponds to the elimination of $H_2S$, of alkyl mercaptan (starting reactant), of the heavy products, and of the traces of volatile compounds, respectively.

Each of these "purification" steps b), c), d) and e) can be carried out according to any methods known to those skilled in the art, such as stripping, distillation, decanting, and the like.

Step f) for eliminating the alkyl hydrodisulphide, giving dialkyl sulphide or dialkyl polysulphides, corresponds, for its part, to a subsequent and separate chemical reaction carried out in the presence of a basic catalyst, and which can be performed after step a), b), c), d) or e), preferably after step a), b), c) or d), preferably after steps b), c) or d), particularly preferably after step d).

Thus, and according to a particularly preferred embodiment, step f) of conversion by basic catalysis is carried out just before final topping step e).

Figure 2:
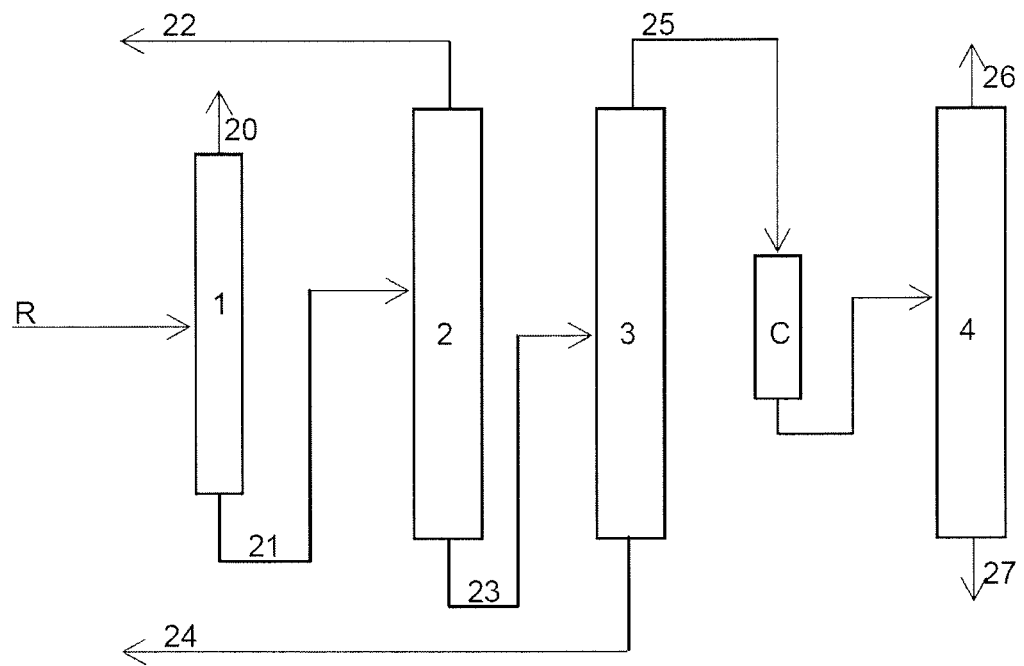
FIG. 2 is a schematic diagram of an industrial apparatus for purifying a dialkyl disulphide synthesis reaction crude having a catalysis reactor.

For the synthesis of dimethyl disulphide, basic catalysis step f) is advantageously performed after heavy product separation step d), i.e. after the heavy product distillation column 6 and before the final distillation column 7 described in FIG. 2 of patent application EP 0 976 726.

Another advantage linked to the process according to the present invention is that it makes it possible to increase the industrial production of dialkyl disulphides. Indeed, in the processes conventionally used today, for example as described in patent application EP 0 976 726, the operator seeks to minimize the formation of organic hydrodisulphide responsible, by self-degradation as indicated above, for the unpleasant odours of said dialkyl disulphides. One means for limiting the formation of hydrodisulphide consists in slowing down the reaction for oxidation of the alkyl mercaptan with sulphur by limiting the rate of introduction of said alkyl mercaptan into the oxidation reaction.

By virtue of the process of the present invention, which consists of adding, to the conventional process, a step of basic catalysis of the reaction crude, enabling conversion of the alkyl hydrodisulphide, it is now possible to increase the rate of introduction of the starting alkyl mercaptan by approximately 30% to 100%. This makes it possible to considerably increase the overall productivity of the industrial synthesis of dialkyl disulphides.

For example, in the case of the synthesis of dimethyl disulphide, the initial flow rate of methyl mercaptan can be increased from approximately 950 g/h (in the conventional process, without basic catalysis for the conversion of the methyl hydrodisulphide) up to approximately 1500 g/h with the additional step of basic catalysis of the reaction crude according to the present invention.

In other words, compared with a synthesis without a "finishing" catalytic reactor, an increase in productivity per $m^3$ of catalyst (of the main reaction of oxidation with sulphur) from approximately 2000 kg/h/$m^3$ of catalyst to approximately 3000 kg/h/$m^3$ of catalyst (of the main reaction of oxidation with sulphur) was observed.

Thus, and according to yet another aspect, the invention consists of the use of at least one basic catalyst on a reaction crude of oxidation of an alkyl mercaptan of formula RSH with sulphur, for increasing the overall productivity of the industrial synthesis of dialkyl disulphides of formula RSSR, in which R is as defined above.

The appended FIG. 1 is a scheme showing an industrial apparatus for purifying a dialkyl disulphide synthesis reaction crude (as described in patent application EP 0 976 726 for the synthesis of dimethyl disulphide, or DMDS).

A degassing column 1 serves to completely eliminate, via the pipe 20, the $H_2S$ dissolved in the reaction crude leaving the reactor, via the pipe R. A distillation column 2 makes it possible to separate out most of the alkyl mercaptan (methyl mercaptan in the case of the synthesis of DMDS) in excess with a view to recycling it via the pipe 22 into the oxidation reaction.

On exiting the column 2, the mixture is brought, via the pipe 23, into the second distillation column 3, where the residual dialkyl polysulphides (dimethyl polysulphides in the case of the synthesis of DMDS) are eliminated at the bottom of the column via the pipe 24 so as to be optionally recycled into the oxidation reaction.

The dialkyl disulphide (for example DMDS), collected at the top of the column 3 via the pipe 25, is introduced into a third distillation column 4 where the volatile impurities, such as methyl mercaptan and dimethyl sulphide (in the case of the synthesis of DMDS) are eliminated at the top of the column via the pipe 26. The dialkyl disulphide (for example DMDS) is collected at the bottom of the column via the pipe 27.

The appended FIG. 2 is a scheme similar to that shown in FIG. 1, with in addition the reactor C for basic catalysis according to the present invention. In FIG. 2, which represents a preferred embodiment of the present invention, the reactor C enabling the basic catalysis is placed between the column 3 and the column 4, i.e. after heavy product separation step d) and before final topping step e).

The present invention is now illustrated by means of the following examples, which are in no way limiting in nature for the invention as claimed in the appended claims.

In these examples, the rate of passage over the basic catalyst for conversion of the alkyl hydrodisulphide, which will be referred to as hourly space velocity (HSV), is expressed in $h^{-1}$ and is equal to the ratio of the hourly space flow rate of reactant to the volume of said basic conversion catalyst.

EXAMPLE 1

Synthesis of DMDS According to EP 0 976 726 with Higher Productivity Conditions, and without Basic Conversion Catalysis (Comparative Example)

a) Equipment:

The appended FIG. 1 is a scheme of the apparatus used, in which a reaction crude results from the reaction for oxidation of methyl mercaptan with sulphur (as described in patent application EP 0 976 726).

A degassing column 1 serves to completely eliminate, via the pipe 20, the $H_2S$ dissolved in the reaction crude leaving the reactor, via the pipe R. A distillation column 2 makes it possible to separate most of the methyl mercaptan in excess with a view to recycling it, via the pipe 22, into the oxidation reaction.

The column 3 makes it possible to separate the residual dimethyl polysulphides (DMPS) with a view to recycling them into the oxidation reactor via the pipe 24.

b) Procedure:

The methyl mercaptan (MM) is introduced, in the liquid state under pressure with a flow rate of 1440 g/h, into the reactor. The liquid sulphur (S) is introduced with a flow rate of 240 g/h into a first reactor (MM/S molar ratio=4).

The oxidation reactor (reaction volume of 300 ml) contains 20 g of dry Amberlyst® A21 resin. The working pressure is maintained at 5.5 bar relative and the temperature at 40° C. The reaction mixture, on leaving this first reactor, is then sent to a degasser in order to be treated.

After treatment, the mixture, freed of the $H_2S$, is sent to a second reactor which contains a charge of 94 g of dry Amberlyst® A21 resin. The pressure in this second reactor is 5.5 bar relative and the temperature is 50° C. On leaving the reactor, the mixture is then introduced into a degasser for elimination of the $H_2S$.

On leaving the degassing column 1, the mixture is introduced into the first distillation column 2, via the pipe 21, in order to eliminate virtually all the methyl mercaptan in excess. This methyl mercaptan can be recycled, via the pipe 22, to the introduction of the reactants into the oxidation reaction. On leaving the column 2, the mixture is brought, via the pipe 23, into the second distillation column 3, where the DMPS are eliminated at the bottom of the column, via the pipe 24, so as to be optionally recycled into the oxidation reaction.

The DMDS, collected at the top of the column 3 via the pipe 25, is introduced into a third distillation column 4, where the volatile impurities such as the methyl mercaptan and the dimethyl sulphide are eliminated at the top of the column via the pipe 26. The DMDS collected at the bottom of the column via the pipe 27 has the following weight composition (all the values are expressed by weight):

| | |
|---|---|
| DMDS: | 99.9% |
| DMTS: | 334 ppm |
| $CH_3SSH$: | 377 ppm |
| MM: | 32 ppm |
| DMS: | <2 ppm (limit of detection) |

This test shows the presence of $CH_3SSH$ in the final product when the synthesis of the DMDS is carried out under conditions of higher productivity than in Patent Application EP 0 976 726 (higher reactant flow rates and oxidation reactor temperature).

EXAMPLE 2

In Accordance with the Present Invention

Take the DMDS crude above of Example 1 containing 377 ppm by weight of $CH_3SSH$. These 337 ppm can give back, over time, 226 ppm of $CH_3SH$ in the final product.

This DMDS is sent to a bed of Amberlyst® A21 basic resin from Rohm & Haas which has been prewashed with methanol and dried so as to eliminate the water contained in this resin (5 g of dry resin, i.e. 14.3 ml), at a rate of 180 g/h (171 ml/h, which results in an HSV of 12 $h^{-1}$) for 2 hours and at a temperature of 40° C. The $CH_3SSH$ is no longer detectable by gas chromatography (limit of detection approximately 2 ppm by weight) at the output of the tubular reactor containing the resin.

EXAMPLE 3

Take another DMDS crude, this time containing 428 ppm of $CH_3SSH$ (these 428 ppm can give back, over time, 257 ppm of $CH_3SH$ in the final product).

This DMDS is sent to a bed of Amberlyst® A21 basic resin from Rohm & Haas which has been predried (5 g, i.e. 14.3 ml), at a rate of 530 g/h (505 ml/h, i.e. an HSV of 35 $h^{-1}$) for 2 hours and at a temperature of 40° C. The $CH_3SSH$ is no longer detectable by gas chromatography (limit of detection approximately 2 ppm by weight) at the output of the tubular reactor containing the resin.

EXAMPLE 4

Take a DMDS crude containing 219 ppm of $CH_3SSH$ (these 219 ppm can give back, over time, 131 ppm of $CH_3SH$ in the final product).

This DMDS is sent to a bed of Amberlyst® A21 basic resin from Rohm & Haas which has been predried (5 g, i.e. 14.3 ml), at a rate of 1000 g/h (952 ml/h, i.e. an HSV of 67 $h^{-1}$) for 2 hours and subsequently at 2000 g/h (1904 ml/h, i.e. an HSV of 133 $h^{-1}$) for 2 hours also, and at a temperature of 40° C.

At these two flow rates, the $CH_3SSH$ is no longer detectable by gas chromatography (limit of detection approximately 2 ppm by weight) at the output of the tubular reactor containing the resin.

EXAMPLE 5

Take a DMDS crude containing 239 ppm of $CH_3SSH$ (these 239 ppm can give back, over time, 140 ppm of $CH_3SH$ in the final product).

This DMDS is sent to a bed of Amberlyst® A21 basic resin from Rohm & Haas which has been predried (5 g, i.e. 14.3 ml), at a rate of 2000 g/h (1904 ml/h, i.e. an HSV of 133 $h^{-1}$) for 2 hours and at a temperature of 20° C.

The $CH_3SSH$ is no longer detectable by gas chromatography (limit of detection: approximately 2 ppm by weight) at the output of the tubular reactor containing the resin.

The DMDS used in this example, which initially contained 441 ppm of dimethyl trisulphide (DMTS), contains 809 ppm thereof after passage over the resin, i.e. an increase of 368 ppm. This value of 368 ppm is very close to the theoretical maximum, which is 376 ppm (value which is obtained when considering that each mole of $CH_3SSH$ has given one mole of DMTS).

The invention claimed is:

1. A process for treating a reaction crude containing alkyl hydrodisulphide impurity and a majority of a dialkyl disulphide obtained by oxidation of at least one alkyl mercaptan with sulphur, the process comprising contacting said reaction crude with at least one basic catalyst in a separate step subsequent to the oxidation of the at least one alkyl mercaptan with sulphur to reduce the content of alkyl hydrodisulphide impurity.

2. The process according to claim 1, wherein the at least one alkyl mercaptan is a compound of formula RSH, and the dialkyl disulphide is a compound of formula RSSR, wherein R represents a linear or branched alkyl radical containing from 1 to 20 carbon atoms, optionally substituted with one or more groups, which may be identical or different, and selected from the group consisting of halogens, amino, alkylamino, dialkylamino, carboxyl, alkylcarbonyloxy, alkoxycarbonyl, hydroxyalkyl, alkoxy, mercaptoalkyl, alkylthio, alkylcarbonylamino and alkylaminocarbonyl.

3. The process according to claim 2, wherein R represents a linear or branched alkyl radical containing from 1 to 10 carbon atoms, optionally substituted with one or more groups, which may be identical or different, and selected from the group consisting of halogens, amino, alkylamino, dialkylamino, carboxyl, alkylcarbonyloxy, alkoxycarbonyl, hydroxyalkyl, alkoxy, mercaptoalkyl, alkylthio, alkylcarbonylamino and alkylaminocarbonyl.

4. The process according to claim 1, wherein the at least one alkyl mercaptan is a compound of formula RSH, and the dialkyl disulphide is a compound of formula RSSR, wherein R represents a linear or branched, unsubstituted alkyl radical containing from 1 to 10 carbon atoms.

5. The process according to claim 4, wherein R represents a linear or branched, unsubstituted alkyl radical containing from 1 to 6 carbon atoms.

6. The process according to claim 4, wherein R represents a linear or branched, unsubstituted alkyl radical containing from 1 to 4 carbon atoms.

7. The process according to claim 1, wherein the at least one alkyl mercaptan is methyl mercaptan, and the dialkyl disulphide is dimethyl disulphide.

8. The process according to claim 1, wherein the basic catalyst is a heterogeneous catalyst with respect to the reaction crude.

9. The process according to claim 1, wherein the basic catalyst is chosen from anion exchange resins, basic catalysts in free amine form, aluminas doped with sodium oxide and/or with potassium oxide, and magnesium oxide (MgO).

10. The process according to claim 9, wherein the basic catalyst is an anion exchange resin.

11. A process for preparing dialkyl disulphide, comprising:
   a) oxidizing an alkyl mercaptan with sulphur, by basic catalysis, to obtain a firs reaction crude containing predominantly the corresponding dialkyl disulphide;
   b) stripping $H_2S$ formed;
   c) distilling residual alkyl mercaptan;
   d) separating polysulphides from the first reaction crude;
   e) final elimination of traces of volatile compounds;
   f) bringing at least one stream selected from the group consisting of streams exiting step a), step b), step c), step d), and step a), into contact with a basic catalyst to eliminate alkyl hydrodisulphide by converting said alkyl hydrodisulphide to dialkyl sulphide or dialkyl polysulphides; and
   g) recovering the dialkyl disulphide containing an alkyl hydrodisulphide content of less than 50 ppm by weight.

12. The process according to claim 11, wherein the alkyl mercaptan is methyl mercaptan and the dialkyl disulphide is dimethyl disulphide.

13. The process according to claim 11, wherein step f) is performed after step a), step b), step c), or step d).

14. The process according to claim 11, wherein step is performed after step b), step c), or step d).

15. The process according to claim 11, wherein step f) is performed after step d).

16. The process according to claim 11, wherein the dialkyl disulphide recovered in step g) contains an alkyl hydrodisulphide content of less than 10 ppm by weight.

17. A method for reducing the formation of alkyl hydrodisulphide during industrial synthesis of dialkyl disulphide of formula RSSR in a reaction crude obtained by oxidation of an alkyl mercaptan of formula RSH with sulphur, comprising:
   contacting at least one basic catalyst with the reaction crude containing the alkyl hydrodisulphide impurity and the dialkyl disulphide of formula RSSR,
   wherein R represents a linear or branched alkyl radical containing from 1 to 20 carbon atoms, optionally substituted with one or more groups, which may be identical or different, and selected from the group consisting of halogens, amino, alkylamino, dialkylamino, carboxyl, alkylcarbonyloxy, alkoxycarbonyl, hydroxyalkyl, alkoxy, mercaptoalkyl, alkylthio, alkylcarbonylamino and alkylaminocarbonyl.

18. The method according to claim 17, wherein R represents a linear or branched alkyl radical containing from 1 to 10 carbon atoms, optionally substituted with one or more groups, which may be identical or different, and selected from the group consisting of halogens, amino, alkylamino, dialkylamino, carboxyl, alkylcarbonyloxy, alkoxycarbonyl, hydroxyalkyl, alkoxy, mercaptoalkyl, alkylthio, alkylcarbonylamino and alkylaminocarbonyl.

19. The method according to claim 17, wherein the alkyl mercaptan is methyl mercaptan and the dialkyl disulphide is dimethyl disulphide.

* * * * *

UNITED STATES PATENT AND TRADEMARK OFFICE
CERTIFICATE OF CORRECTION

PATENT NO. : 8,987,519 B2  
APPLICATION NO. : 13/877016  
DATED : March 24, 2015  
INVENTOR(S) : Fremy et al.

Page 1 of 1

It is certified that error appears in the above-identified patent and that said Letters Patent is hereby corrected as shown below:

On the Title Page, Item [56],

"2001/0976726" should read -- 2001/0005766 --

Signed and Sealed this  
Third Day of November, 2015

Michelle K. Lee  
*Director of the United States Patent and Trademark Office*